United States Patent [19]

Hoelderich et al.

[11] Patent Number: 4,933,487

[45] Date of Patent: Jun. 12, 1990

[54] PREPARATION OF 4-PENTENATES

[75] Inventors: Wolfgang Hoelderich, Frankenthal; Heinrich Aichinger; Fritz Naeumann, both of Mannheim; Rolf Fischer, Heidelberg, all of Fed. Rep. of Germany

[73] Assignee: BASF Aktiengesellschaft, Ludwigshafen, Fed. Rep. of Germany

[21] Appl. No.: 327,408

[22] Filed: Mar. 22, 1989

Related U.S. Application Data

[63] Continuation of Ser. No. 115,966, Nov. 2, 1987, abandoned.

[30] Foreign Application Priority Data

Nov. 7, 1986 [DE] Fed. Rep. of Germany ....... 3638011

[51] Int. Cl.$^5$ .................. C07C 67/333; C07C 69/533
[52] U.S. Cl. ...................................... 560/205; 502/61; 502/64; 502/65; 502/66; 502/71
[58] Field of Search .................... 560/205; 502/64, 65, 502/66, 61, 71

[56] References Cited

U.S. PATENT DOCUMENTS 4,332,966  6/1982  Isogai et al. .................... 560/206
4,401,637  8/1983  Marosi et al. .................... 423/329
4,529,815  7/1985  Schneider et al. ............... 560/205

FOREIGN PATENT DOCUMENTS 0046504  3/1982  European Pat. Off.

OTHER PUBLICATIONS

Bull. of the Chem. Soc. of Japan, vol. 46, p. 548.
Tetrahedron, vol. 28, pp. 5769–5777, (1972).
Ullmanns Encyclopadie d. techn. Chemie, 4. Auflage, vol. 24, p. 575 (1983).
"Catalysis by Zeolites", vol. 5, Studies in Surface and Catalysis, ed. B. Imelik et al., Elsevier Scientific Publishing Comp. 1980, p. 203.
"Crystal Structures of Ultra–Stable Faujasites", Advances in Chemistry Series Nr. 101, American Chemical Society Washington, DC, p. 226 ff (1971).

Primary Examiner—Vivian Garner
Attorney, Agent, or Firm—Keil & Weinkauf

[57] ABSTRACT

In an improved process for preparing 4-pentenates by isomerization, where isomeric pentenates are treated at elevated temperatures with zeolites and 4-pentenates are distilled out of the reaction mixture, the improvement comprises using pentenates in mixture with alkanols.

4 Claims, No Drawings

PREPARATION OF 4-PENTENATES

This application is a continuation of application Ser. No. 115,966 filed on Nov. 2, 1987, now abandoned.

In the preparation of pentenates by reaction of butadiene with carbon monoxide and alcohols in the presence of metal carbonyl catalysts, as described for example in German Laid-Open Application DOS 3,040,432, substantial amounts of isomeric pentenates are obtained. For further reactions, for example for preparing a 5-formyl valerate by hydroformylation of a pentenate, however, the preferred starting compound is a 4-pentenate. For that reason, attempts have been made in the past to obtain 4-pentenates by isomerization of isomeric pentenates. As is known from Bull. Chem. Soc. Japan 46,528, however, isomerizing methyl 3-pentenate in the presence of cobalt carbonyls predominantly produces methyl 2-pentenate. It is true that in a method described in Tetrahedron 28 (1972), 5769-77, it is possible, in the presence of a complex of rhodium triphenylphosphine and tin chloride, to shift the isomer equilibrium in such a way that 4-pentenates are obtained. However, the catalyst used therein becomes inactive within a few hours.

EP Application No. 226,349 describes a process for preparing 4-pentenates from a pentenate mixture by a treatment with acid zeolites which contain palladium, ruthenium or rhodium. However, the catalyst life is still in need of improvement.

In the isomerization of pentenates, at thermodynamic equilibrium five isomers are present: 4-pentenate, cis- and trans-3-pentenate and cis- and trans-2-pentenate, the equilibrium being strongly shifted toward the trans-2-pentenate.

It is an object of the present invention to provide a process for preparing a 4-pentenate from isomeric pentenates wherein the catalyst used has a long life and is easily regenerable and, in addition, the linear shift in the double bond to the 4-pentenate takes place preferentially and, what is more, the amount of cis-2-pentenate formed, which is difficult to separate off, is minimal.

We have found that this object is achieved by a process for preparing a 4-pentenate by isomerizing an isomeric pentenate by treatment with a zeolite at elevated temperatures and removal of the 4-pentenate from the reaction mixture by distillation, which comprises using a pentenate in a mixture with an alkanol.

The novel process has the advantage that the addition of an alcohol to the pentenate increases the time on stream of the zeolite catalyst.

Advantageously, the starting point is an isomeric pentenate, for example a 2- or 3-pentenate, which is derivable from an alkanol having not more than 12 carbon atoms. Particular preference is given to using an isomeric alkyl pentenate, in particular of an alkanol having not more than 4 carbon atoms. Suitable starting materials are for example methyl 3-pentenate, ethyl 3-pentenate, propyl 3-pentenate, butyl 3-pentenate, methyl 2-pentenate, ethyl 2-pentenate and propyl 2-pentenate. It is also possible to use a mixture of isomeric pentenates as obtained in the reaction of butadiene with carbon monoxide and alcohols in the presence of a metal carbonyl as described in German Laid-Open Application DOS 3,040,432. Particular preference is given to 3-pentenates.

The isomerization is carried out in the presence of an alkanol of in particular 1 to 6 carbon atoms. Suitable alkanols are for example methanol, ethanol, propanol, butanol, isopropanol or isobutanol, secondary butanols, n-pentanol and n-hexanol. Particularly suitable alkanols have not more than 3 carbon atoms, for example methanol, ethanol and propanols.

The catalyst used for the process according to the invention is a zeolite in the acidic form. Zeolites are crystalline aluminosilicates which have a highly ordered structure comprising a rigid three-dimensional network of $SiO_4$ and $AlO_4$ tetrahedra linked by common oxygen atoms. The ratio of the Si and Al atoms:oxygen is 1:2 (see Ullmann's Encyclopadie d. techn. Chemie, 4th edtn., vol.24, p.575 (1983). The electrovalence of the aluminum-containing tetrahedra is balanced by the inclusion in the crystal of cations, for example an alkali metal or hydrogen ion. Cation exchange is possible. The spaces between the tetrahedra are occupied by water molecules prior to dehydration through drying or calcination.

In the zeolites, the aluminum in the lattice can be replaced by other elements such as B, Ga, Fe, Cr, V, As, Sb, Bi or Be or mixtures thereof, or the silicon can be replaced by a tetravalent element such as Ge, Ti, Zr or Hf.

According to their structure, zeolites are divided into various groups (see Ullmann's Encyclopadie d. techn. Chemie, 4th edtn., vol.24, p.575 (1983)). For instance, the zeolite structure is formed in the mordenite group by tetrahedra arranged in chains and in the chabasite group by tetrahedra arranged in layers, while in the faujasite group the tetrahedra form polyhedra, for example in the form of a cuboctahedron which is composed of tetragons and hexagons. Depending on the way the cuboctahedra are linked, which produces differently sized voids and pores, zeolites are classed as type A, L, X or Y.

Catalysts suitable for the process according to the invention are zeolites from the mordenite group or narrow-pored zeolites of the erionite or chabasite type or zeolites of the faujasite type, for example Y-, X- or L-zeolites. This group of zeolites also includes the ultrastable zeolites of the faujasite type, i.e. dealuminized zeolites. Methods for preparing such zeolites are described in Catalysis by Zeolites, volume 5 of Studies, in Surface Science and Catalysis, ed. B. Imelik et al., Elsevier Scientific Publishing Comp. 1980, p.203, and Crystal Structures of Ultra-stable Faujasites, Advances in Chemistry Series No. 101, American Chemical Society Washington D.C., pp.226 et seq. (1971) and in U.S. Pat. No. 4,512,961.

Zeolites of the pentasil type are particularly advantageous. Their common feature is a pentagon composed of $SiO_4$ tetrahedra. They are characterized by a high $SiO_2/Al_2O_3$ ratio and by pore sizes between those of the zeolites of type A and those of type X or Y (cf. Ullmann's Encyclopädie d. techn. Chem., 4th edtn, vol. 24, p.575 (1983)).

These zeolites can have different chemical compositions. They can be aluminosilicate, borosilicate or iron, beryllium, gallium, chromium, arsenic, antimony or bismuth silicate zeolites or mixtures thereof and aluminogermanate, borogermanate and gallium or iron germanate zeolites or mixtures thereof.

Suitable for the process of the invention are in particular aluminosilicate, borosilicate and iron silicate zeolites of the pentasil type. The aluminosilicate zeolite is prepared for example from an aluminum compound, preferably $Al(OH)_3$ or $Al_2(SO_4)_3$, and a silicon component, preferably finely divided silicon dioxide, in an aqueous amine solution, in particular in polyamines such as 1,6-hexanediamine or 1,3-propanediamine or triethylenetetramine solution, in the presence or in particular in the absence of alkali metal or alkaline earth metal at from 100° to 220° C. under autogenous pressure. This also includes the isotactic zeolites described in German Laid-Open Application DOS 3,006,471. The aluminosilicate zeolites obtained have an $SiO_2/Al_2O_3$ ratio of from 10 to 40,000, depending on the mixing ratio of the starting materials. These aluminosilicate zeolites can also be synthesized in an ether medium such as diethylene glycol dimethyl ether, in an alcohol medium such as methanol or 1,4-butanediol, or in water.

Borosilicate zeolites can be synthesized under autogenous pressure, for example at from 90° to 200° C., by reacting a boron compound, for example $H_3BO_3$, with a silicon compound, preferably finely divided silicon dioxide in an aqueous amine solution, in particular in 1,6-hexanediamine, 1,3-propanediamine or triethylenetetramine solution, in the presence or in particular in the absence of alkali metal or alkaline earth metal. They also include the diamine, 1,3-propanediamine or triethylenetetramine solution, in the presence or in particular in the absence of alkali metal or alkaline earth metal. They also include the isotactic zeolites described in German Laid-Open Application Dos 3,006,471 and- EP 46,504. These borosilicate zeolites can also be prepared by carrying out the reaction not only in aqueous amine solution but alternatively in an ether solution, for example diethylene glycol dimethyl ether, or in an alcohol solution, for example 1,6-hexanediol.

The iron silicate zeolite is obtained for example from an iron compound, preferably $Fe_2(SO_4)_3$, and a silicon compound, preferably finely divided silicon dioxide in an aqueous amine solution, in particular 1,6-hexanediamine, in the presence or absence of alkali metal or alkaline earth metal at from 100° to 200° C. under autogenous pressure.

The high-silicon zeolites used ($SiO_2/Al_2O_3 \geq 10$) also include the conventional ZSM types, ferrierite, Nu-1 and Silicalite ®.

The aluminosilicate, borosilicate and iron silicate zeolites thus prepared, after they have been isolated, dried at from 100° to 160° C., preferably at 110° C., and calcined at from 450° to 550° C., preferably at 500° C., can be combined with a binder in a ratio of from 90:10 to 40:60% by weight and molded into extrudates or tablets. Suitable binders are various aluminum oxides, preferably boehmite, amorphous aluminosilicates having an $SiO_2/Al_2O_3$ ratio of from 25 : 75 to 90 : 5, preferably 75 : 25, silicon dioxide, preferably finely divided $SiO_2$, mixtures of finely divided $SiO_2$ and finely divided $Al_2O_3$, $TiO_2$, $ZrO_2$, and clay. After molding, the extrudates or tablets are dried at 110° C. for 16 hours and calcined at 500° C. in 16 hours.

It is also possible to obtain advantageous catalysts by molding the isolated aluminosilicate or borosilicate zeolite immediately after drying and subjecting it to calcination only after the molding. The aluminosilicate and borosilicate zeolites prepared can be used in the pure form, without binder, as extrudates or tablets, with oxalic acid, acetic acid, nitric acid, ammonia, amines, silicoesters and graphite or mixtures thereof.

If the zeolite, on account of its manner of preparation, is present not in the advantageously catalytically active, acidic H-form but, for example, in the Na-form, it can be completely or partially converted into the desired H-form by ion exchange, for example with ammonium ions, and subsequent calcination, or by treatment with acids.

Should the zeolitic catalyst used according to the invention undergo deactivation due to coking, it is advisable to regenerate the zeolite by burning off the coke deposit with air or with an air/$N_2$ mixture at from 400 to 550° C., preferably at 500° C. This restores the initial activity level of the zeolite.

By precoking it is possible to set the activity of the catalyst for optimum selectivity in respect of the desired reaction product.

To obtain a high selectivity, high conversions and long times on stream, it is advantageous to modify the zeolites. A suitable method of modifying the catalysts comprises for example doping the shaped or unshaped zeolite with metal salts by ion exchange or impregnation. The metals used are alkali metals such as Li, Cs or K, alkaline earth metals such as Mg, Ca or Sr, metals of main groups III, IV and V, such as Al, Ga, Ge, Sn, Pb or Bi, transition metals of subgroups IV–VIII, such as Ti, Zr, V, Nb, Cr, Mo, W, Mn, Re, Fe, Ru, Os, Co, Rh, Ir, Ni, Pd or Pt, transition metals of sub groups I or II, such as Cu, Ag or Zn, and rare earth metals such as La, Ce, Pr, Nd, Fr, Yb or U. Advantageously, the metals mentioned are present in from 0.1 to 5% weight.

Advantageously, doping is carried out by introducing the molded zeolite into a riser pipe and passing an aqueous or ammoniacal solution of a halide or nitrate of one of the abovementioned metals over it at from 20° to 100° C. Such an ion exchange can take place with, for example, the hydrogen, ammonium, or alkali metal form of the zeolite. Another way of applying metal to the zeolite comprises impregnating the zeolitic material with, for example, a halide, nitrate or oxide of one of the abovementioned metals in aqueous, alcoholic or ammoniacal solution. Both ion exchange and impregnation are followed by at least a drying step, optionally by repeated calcination.

A possible embodiment comprises for example dissolving $Cu(NO_3)_2 \times 3\ H_2O$ or $Ni(NO_3)_2 \times 6\ H_2O$ or $Ce(NO_3)_2 \times 6\ H_2O$ or $La(NO_3)_2 \times 6\ H_2O$ or $Cs_2CO_3$ in water and impregnating the molded or unmolded zeolite with this solution for a certain period, for example 30 minutes. Any supernatant solution is stripped of water in a rotary evaporator. The impregnated zeolite is then dried at about 150° C. and calcined at about 550° C. This impregnating step can be carried out several times in succession until the desired metal content is obtained.

It is also possible to prepare, for example an aqueous $Ni(NO_3)_2$ solution or ammoniacal P solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

An ion exchange on the zeolite present in the H-form or ammonium form or alkali metal form can be carried out by introducing the zeolite in extruded or pellet form into a column and for example passing an aqueous $Ni(NO_3)_2$ solution or ammoniacal $Pd(NO_3)_2$ solution over it in a recycle loop and at a slightly elevated temperature of from 30° to 80° C. for from 15 to 20 hours. This is followed by washing out with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the zeolitic material, which may be in molded or unmolded form, with an acid such as hydrochloric acid, hydrofluoric acid or phosphoric acid and/or steam, advantageously, for example, by treating the zeolite in pulverulent form with 1 N phosphoric acid at 80° C. for 1 hour and then washing with water, drying at 110° C. for 16 hours and calcining at 500° C. in 20 hours.

Alternatively, before or after being molded together with a binder, the zeolite is treated for example at from 60 to 80° C. with from 3 to 25 % strength by weight, in particular from 12 to 20% strength by weight, aqueous hydrochloric acid for from 1 to 3 hours. Afterwards, the zeolite thus treated is washed with water, dried and calcined at from 400° C. to 500° C.

In a particular embodiment, the acid treatment comprises treating the zeolitic material, before it is molded, with hydrofluoric acid, generally in the form of 0.001 N to 2 N, preferably 0.05 N to 0.5 N, hydrofluoric acid, at an elevated temperature, for example by heating under reflux for, in general, from 0.5 to 5, preferably from 1 to 3, hours. After the zeolitic material has been isolated, for example by filtering and washing, it is advantageously dried, for example at from 100° to 160° C., and calcined, in general at from 450° C. to 600° C. In a further preferred form of the acid treatment, the zeolitic material, after it has been molded together with a binder, is treated at an elevated temperature, advantageously at from 50° to 90° C., preferably at from 60° to 80° C., for from 0.5 to 5 hours with, preferably, from 12 to 20% strength by weight hydrochloric acid. The zeolitic material is, in general, subsequently washed, expediently dried at from 100° to 160° C. and calcined at, in general, from 450° to 600° C. An HF treatment can also be followed by an HCl treatment.

The catalysts described here can optionally be used, for example, in the form of from 2 to 4 mm extrudates or as tablets from 3 to 5 mm in diameter or as chips having particle sizes of from 0.1 to 0.5 mm, or in a fluidizable form.

The process according to the invention is advantageously carried out under the following reaction conditions:

The molar ratio of pentenate:alkanol advantageously ranges from 1:0.1 to 1:10, in particular from 1:0.2 to 1:3.

The isomerization is advantageously carried out at from 50° to 300° C. It is generally carried out under atmospheric pressure, subatmospheric pressure or, alternatively, superatmospheric pressure, for example at not more than 50 bar.

In a batchwise method of working the process, for example, a pulverulent zeolite is suspended in a stirred vessel in the isomeric pentenate-alkanol mixture and stirred at from 50° to 250° C., in particular from 100 to 200oC, for from 2 to 20 hours. After the catalyst has been separated off, methyl 4-pentenate is isolated by distillation.

In a preferred, continuous method of working the process, a molded zeolite catalyst is introduced into a reaction tube and the mixture of isomeric pentenate and alkanol to be isomerized is pumped in liquid form through the tube at from 50 to 250oC, in particular at from 100° to 200° C., preferably at 100° to 150° C., for an average residence time of from 5 to 100 minutes. The reaction mixture is then separated in a conventional manner, for example by distillation, and unconverted starting material is advantageously recycled.

In a particularly preferred embodiment of the process according to the invention, isomeric pentenate and alkanol are passed in gas form, if desired together with an inert carrier gas such as nitrogen, over the zeolite catalyst. In this process, the temperature is advantageously maintained at from 150° to 300° C., in particular from 150° to 250° C. It has proven advantageous to maintain a WHSV (g of feed mixture per g of catalyst per hour) of from 0.1 to 20 $h^{-1}$, in particular from 0.5 to 5 $h^{-1}$. The gaseous reaction mixture obtained is condensed and methyl 4-pentenate is isolated by distillation.

4-Pentenates obtainable by the process according to the invention are suitable for preparing 5-formyl valerates, an intermediate for preparing e-caprolactam, hexanediol or adipic acid.

The process is illustrated in the Examples below.

EXAMPLES 1-5

The reactions are carried out in the gas phase in a tubular reactor (helix, internal diameter 0.6 cm, length 90 cm) under isothermal conditions for not less than 6 hours. The reaction products are separated off and characterized in a conventional manner. The reaction products and starting materials are quantitatively determined by gas chromatography in a conventional manner. Reaction conditions and results are given in Table 1.

The catalysts used for the process according to the invention in the Examples are:

Catalyst A

The borosilicate zeolite of the pentasil type is prepared in a hydrothermal synthesis from 640 g of finely divided $SiO_2$, 122 g of $H_3BO_3$, 8 kg of an aqueous 1,6-hexanediamine solution (mixture 50:5% by weight) at 170° C. under autogenous pressure in a stirred autoclave. After filtering and washing, the crystalline reaction product is dried at 100° C./24 h and calcined at 500° C./24 h. This borosilicate zeolite comprises 94.2% by weight of $SiO_2$ and 2.3% by weight of $B_2O_3$.

This material is molded with molding aids into 2 mm extrudates which are dried at 110° C./16 h and calcined at 500° C./24 h.

Catalyst A is obtained by impregnating the above extrudates with a $Pd(NO_3)_2/NaNO_3$ solution. After drying at 130° C./2 h and calcination at 540° C./2 h the Pd content is 2.5% by weight and the Na content 1.0% by weight.

Catalyst B

Catalyst B is obtained in the same way as catalyst A except that the Pd content is 0.5% by weight and the Na content 1.0% by weight.

Catalyst C

Commercially obtainable Na-Y zeolite is ion exchanged with aqueous $(NH_4)_2SO_4$ solution in a conventional manner until the Na content is less than 0.05% by weight (after drying at 110° C./2 h and calcination at 570° C./3 h). The powder thus obtained is molded with molding aids into extrudates which are dried at 110° C. and calcined at 500° C./16 h.

Catalyst D

Commercially obtainable Na-Y zeolite is extruded with boehmite in a weight ratio of 60:40, dried at 110°

C. and calcined at 500° C./16 h and subjected to ion exchange with 20% strength ammonium chloride solution. The residual sodium content is 0.2% by weight (calcined at 500° C.).

These extrudates are impregnated with aqueous Co(NO$_3$)$_2$ solution in a conventional manner. After drying at 110° C. and calcination at 540° C./2 h the Co content is 1.5% by weight.

Catalyst E

Catalyst E is obtained by impregnating catalyst C with aqueous Pd(NO$_3$)$_2$ solution as described in the case of catalyst A. The Pd content is 0.4% by weight.

The results obtained with the above catalysts and the reaction conditions are given in Table 1.

TABLE 1

Isomerization of methyl 3-pentenate (PSE)/CH$_3$OH

| | Example | | | | |
|---|---|---|---|---|---|
| | 1 | 2 | 3 | 4 | 5 |
| 3-PSE/CH$_3$OH molar | 1:0.5 | 1:0.5 | 1:0.75 | 1:0.5 | 1:0.75 |

| Catalyst | A | B | C | D | E |
|---|---|---|---|---|---|
| Temperature | 180° C. | 180° C. | 180° C. | 180° C. | 180° C. |
| WHSV | 1.3 h$^{-1}$ | 1.3 h$^{-1}$ | 1.3 h$^{-1}$ | 1.3 h$^{-1}$ | 1.3 h$^{-1}$ |
| Liquid output contains in % by volume | | | | | |
| 4-PSE | 7.7 | 4.8 | 7.8 | 7.0 | 9.2 |
| 3-PSE | 69.3 | 89.3 | 66.3 | 80.0 | 62.8 |
| 2-PSE | 7.5 | 3.9 | 6.0 | 3.1 | 13.2 |

EXAMPLES 6-11

In Examples 6-11 it is shown that the addition of methanol to the methyl pentenate used produces a bigger improvement in catalyst life than the addition of other organic solvents. These experiments were carried out on catalyst F. The reaction conditions and results are given in Table 2.

Catalyst F

Catalyst F is obtained by molding the borosilicate zeolite prepared in catalyst A with boehmite in a weight ratio of 60:40 into 2 mm extrudates, which are dried at 130° C. and calcined at 500° C./16 h. These extrudates are impregnated with an aqueous Pd(NO$_3$)$_2$ solution in a conventional manner. After further drying at 130° C. and calcination at 540° C./2 h the Pd content is 1.3% by weight and the Ca content is 0.3% by weight.

The experimental results and the experimental conditions are set out in Table 2.

TABLE 2

| | Example | | | | | |
|---|---|---|---|---|---|---|
| | 6 | 7 | 8 comparison | 9 comparison | 10 comparison | 11 comparison |
| LM$^1$ | CH$_3$OH | CH$_3$OH | toluene | toluene | THF | THF |
| 3-PSE/LM$^2$ | 1:1 | 1:1 | 1:0.3 | 1:0.3 | 1:0.5 | 1:0.5 |
| Temperature | 180° C. | 180° C. | 180° C. | 180° C. | 180° C. | 180° C. |
| WHSV | 0.4 h$^{-1}$ | 0.4 h$^{-1}$ | 0.4 h$^{-1}$ | 0.4 h$^{-1}$ | 0.4 h$^{-1}$ | 0.4 h$^{-1}$ |
| Time$^3$ | 26 h | 102 h | 26 h | 102 h | 26 h | 102 h |
| The liquid output contains in % by volume | | | | | | |
| 4-PSE | 7.3 | 8.3 | 3.9 | 1.8 | 3.3 | 1.6 |
| 3-PSE | 55.3 | 67.8 | 78.3 | 94.4 | 92.7 | 93.4 |
| 2-PSE | 25.5 | 17.4 | 3.9 | 2.1 | 2.3 | 1.4 |

$^1$LM = solvent
$^2$molar ratio
$^3$time of sampling

EXAMPLES 12-14

Examples 12-14 illustrate the improvement obtainable in the time on stream by adding methanol. Catalyst G is used here.

Catalyst G

The borosilicate zeolite extrudates described in catalyst A are introduced into a riser tube and ion exchanged with a 20% strength aqueous NH$_4$CL solution at 80° C./2 h. An ammoniacal Pd(NO$_3$)$_2$ solution (11% by weight of Pd) is then passed over. After drying at 110° C. and calcination at 500° C./5 h the pd content is 2% by weight.

The results obtained and the experimental parameters are summarized in Table 3.

TABLE 3

Isomerization of methyl 3-pentenate (3 PSE)/CH$_3$OH mixtures

| | Example | | | | | | | | | |
|---|---|---|---|---|---|---|---|---|---|---|
| | 12 | | | 13 | | | 14 | | | |
| 3-PSE/LM$^1$ | 1:0 | | | 1:1 | | | 1:2 | | | |
| Temperature | 180° C. | | | 180° C. | | | 180° C. | | | |
| WHSV | 1.3 h$^{-1}$ | | | 1.3 h$^{-1}$ | | | 1.3 h$^{-1}$ | | | |
| Time | 3 h | 11 h | 40 h | 3 h | 11 h | 40 h | 120 h | 3 h | 11 h | 40 h | 120 h |
| PSE content in liquid output in % by volume | | | | | | | | | | |
| 4-PSE | 10.0 | 4.4 | 1.4 | 10.0 | 9.8 | 6.8 | 5.0 | 9.1 | 8.8 | 9.0 | 7.6 |

$^1$molar ratio

We claim:

1. In a process for preparing a 4-pentenoic acid C$_1$ to C$_4$ alkylester by isomerizing a pentenate selected from the group consisting of 3pentenoic acid C$_1$ to C$_4$ alkyl ester, 2-pentenoic acid C$_1$ to C$_4$ alkyl ester and mixtures thereof by treatment with a zeolite in acidic form at a temperature of from 50 to 300° C. and removing the resulting 4-pentenoic acid C$_1$ to C$_4$ alkyl ester by distillation from the reaction mixture, the improvement which comprises carrying out the isomerization in the presence of an alkanol having from 1 to 3 carbon atoms, the molar ratio of pentenate:alkanol ranging from 1:01 to 10.

2. A process as claimed in claim 1, wherein the catalyst used is a zeolite of the pentasil type.

3. A process as claimed in claim 1, wherein the catalyst used is a zeolite of the faujasite type.

4. A process as claimed in claim 1, wherein the zeolite used has a noble metal or other transition metal of subgroups I, II or IV-VIII content.

* * * * *